(12) United States Patent
Jensen

(10) Patent No.: US 6,859,659 B1
(45) Date of Patent: Feb. 22, 2005

(54) ESTIMATION OF VECTOR VELOCITY

(75) Inventor: Jørgen Arendt Jensen, Lyngby (DK)

(73) Assignee: B-K Medical A/S, Gentofte (DE)

( * ) Notice: Subject to any disclaimer, the term of this patent is extended or adjusted under 35 U.S.C. 154(b) by 0 days.

(21) Appl. No.: 09/959,883

(22) PCT Filed: May 10, 2000

(86) PCT No.: PCT/DK00/00243

§ 371 (c)(1),
(2), (4) Date: Nov. 9, 2001

(87) PCT Pub. No.: WO00/68678

PCT Pub. Date: Nov. 16, 2000

(30) Foreign Application Priority Data

May 10, 1999  (DK) ........................................ 1999 00633

(51) Int. Cl.[7] .................................................. A61B 8/06

(52) U.S. Cl. ........................ 600/407; 600/437; 342/108; 367/89

(58) Field of Search ................................ 600/407, 437, 600/443, 447, 453–456; 73/861.25, 861.27, 861.31; 367/89, 100, 125, 90; 250/201.9; 340/936, 951, 953, 957; 356/121; 342/104–105, 107–108, 117

(56) References Cited

U.S. PATENT DOCUMENTS

| 5,000,184 | A   |   | 3/1991  | Bonnefous ............. 128/661.09 |
| 5,249,577 | A   | * | 10/1993 | Shinomura et al. ......... 600/447 |
| 6,148,224 | A   | * | 11/2000 | Jensen ........................ 600/407 |
| 6,270,459 | B1  | * | 8/2001  | Konofagu et al. ........... 600/449 |
| 6,725,076 | B1  | * | 4/2004  | Jensen ........................ 600/407 |

FOREIGN PATENT DOCUMENTS

| JP | 09257818    | 10/1997 |
| WO | WO 98/00719 | 1/1998  |

OTHER PUBLICATIONS

D.J. Phillips et al. , "Should Results of Ultrasound Doppler Studies by Reported in Units of Frequency or Velocity?" *Ultrasound Med. Boil.*, 15:205–212, 1989.

M.D. Fox, "Multiple Crossed–Beam Ultrasound Doppler Velocimetry," *IEEE Trans. Son. Ultrason.*, SU–25:281–286, 1978.

G.E. Trahey et al., "Angle Independent Ultrasonic Detection of Blood Flow," *IEEE Trans. Biomed. Eng.*, BME–34:965–967, 1987.

V.L. Newhouse et al., "Ultrasound Doppler Probing of Flows Transverse with Respect to Beam Axis," *IEEE Trans. Biomed Eng.*, BME–34:779–788, 1987.

J.A. Jensen et al., "A New Method for Estimation of Velocity Vectors," *IEEE trans. Ultrason., Ferroelec., Freq. Contr.*, 45:837–851, 1998.

J.A. Jensen, *Estimation of Blood Velocities Using Ultrasound: A Signal Processing Approach*, Cambridge University Press, New York, 1996.

P. Munk et al., "Performance of a vector velocity estimator," *IEEE Ultrason. Symp.*, pp. 1489–1493, 1998.

C. Kasai et al., "Real–Time Two–Dimensional Blood Flow Imaging Using an Autocorrelation Technique," *IEEE Trans. Son. Ultrason.*, 32:458–463, 1985.

(List continued on next page.)

*Primary Examiner*—Francis J. Jaworski
(74) *Attorney, Agent, or Firm*—Finnegan, Henderson, Farabow, Garrett & Dunner, L.L.P.

(57) ABSTRACT

A method and apparatus are provided for estimating the velocity vector of a remotely sensed object or group of objects using either ultrasound or electromagnetic radiation. The movement of the object is determined by emitting and receiving a pulsed field with spatial oscillations in both the axial and transverse directions. Using a number of pulsed emissions and the transverse spatial oscillations the received signal is influenced by transverse motion and a new autocorrelation estimator is used for determining the velocity vector.

11 Claims, 9 Drawing Sheets

OTHER PUBLICATIONS

J.A. Jensen et al., "Calculation of Pressure Fields from Arbitrarily Shaped, Apodized, and Excited Ultrasound Transducers," *IEEE Trans. Ultrason. Ferroelec., Freq. Contr.*, 39:262–267, 1992.

J.A Jensen, "Field: A Program for Simulating Ultrasound Systems," *Medm. Biol. Eng. Comp.*, 10th Nordic–Baltic conference on Biomedical Imaging, vol. 4, Supplement 1, Part 1:351–353, 1996b.

* cited by examiner

ESTIMATION OF VECTOR VELOCITY

FIELD OF THE INVENTION

The invention relates to a method and an apparatus for estimating the velocity vector of a remotely sensed object or group of objects using either sound, in particular ultrasound, or electro-magnetic radiation, eg radar. The movement of the object is determined by emitting and receiving a pulsed field with spatial oscillations in both the axial direction of the transducer and in one or two directions transverse to the axial direction. By using a number of pulse emissions, the inter pulse movement can be estimated and the velocity found from the estimated movement and the time between pulses. The invention is based on the principle of using transverse spatial oscillations for making the received signal influenced by transverse motion, and then using a new autocorrelation estimator for determining the velocity vector. The estimator uses fourth order moments rather than second order moments. The estimation process can also be optimized by using lags different from 1 (one), compensating for the lateral and axial frequencies, and by averaging RF samples.

BACKGROUND OF THE INVENTION

Figure 1:
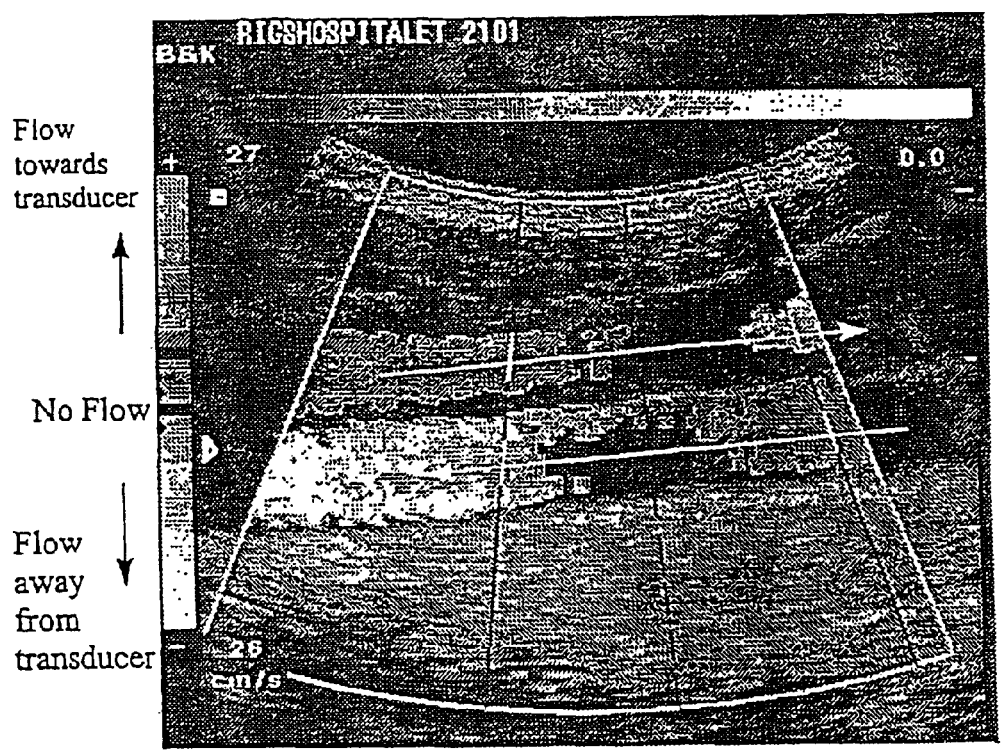
Figure 1A:
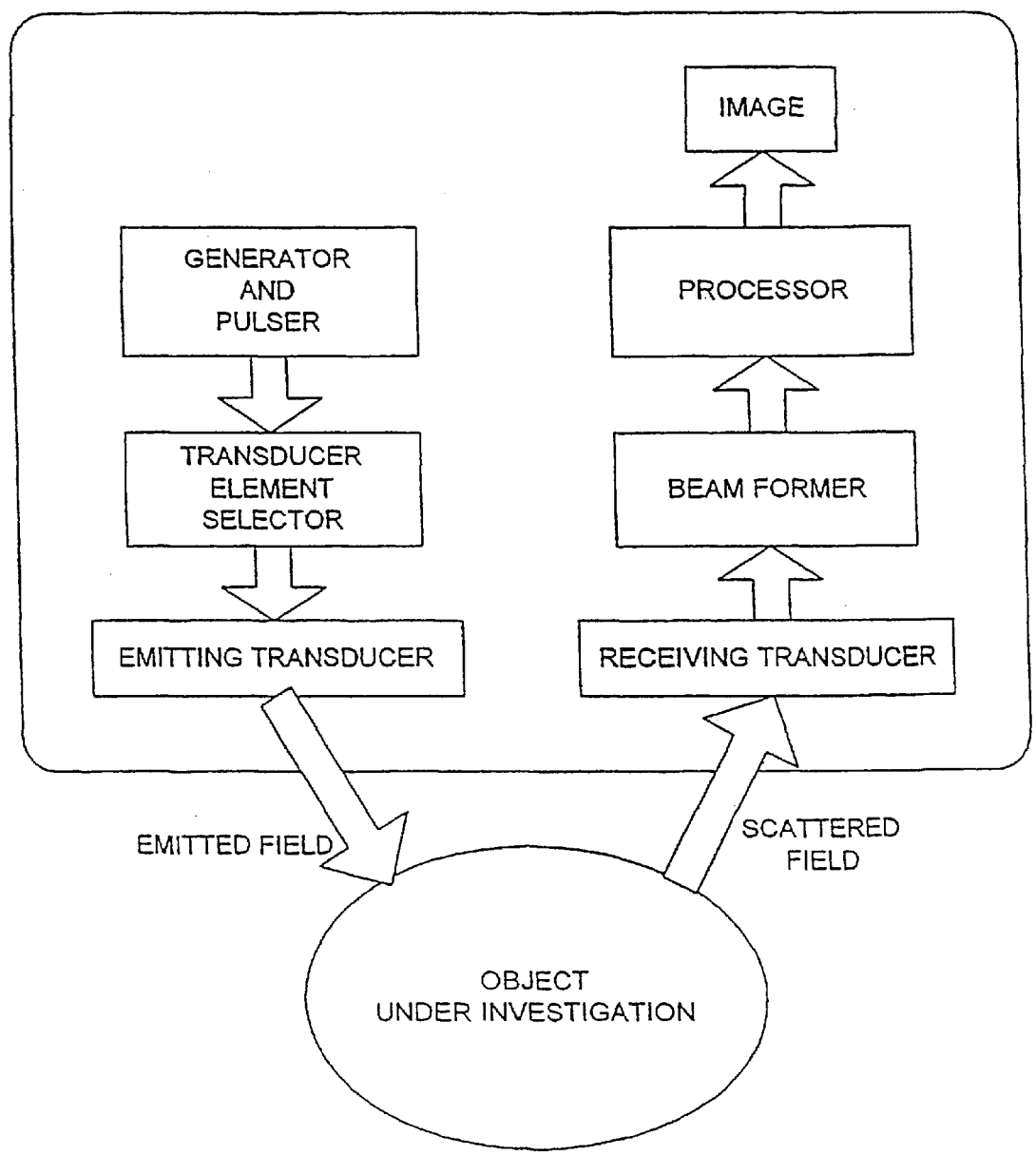

Medical ultrasound is extensively used for studying flow dynamics in the human body by using color flow mapping. The technique displays a color image of the flow superimposed on the normal anatomic B-mode image. The velocity component along the ultrasound beam direction is measured, and a flow transverse to the beam is not displayed. This is shown in FIG. 1, where the flow in the carotid artery and the jugular vein is displayed. The image is acquired with a convex array, and the angles between flow direction and the ultrasound beam changes over the image. Notice the chance of estimated flow direction around the dashed line in both vessels due to the change of angle between the flow and the ultrasound beam. This is one of the main limitations of current ultrasound flow systems, since most vessels are parallel to the skin surface, and therefore it is a problem to get a sufficiently small angle between the flow and the beam. Also the flow is often not parallel to the vessel surface, and it is therefore difficult, if not impossible, to estimate the correct angle and compensate for it [1].

Several authors have attempted to remedy this artifact. Fox [2] suggested using two beams to find the transverse component. The system works well for large transducers and investigations close to the transducer, but the variance of the transverse component increases for situations with large depths and smaller transducers as used in cardiac scanning through the ribs. Trahey and co-workers [3] have suggested using speckle tracking in which a small search region in one image is correlated or compared to a subsequent image. This approach has problems in terms of frame rate, since images are compared, and the resolution of the velocity estimates can be low. Newhouse et al [4] developed a method in which the total bandwidth of the received signal is affected by the transverse velocity. It is, however, often difficult to find this bandwidth due to the inherent noise in the signal.

In this invention a new and improved estimator is presented for the approach described previously in [5] and [6], which makes it possible to estimate the flow vector using a transversally modulated probing field.

SUMMARY OF THE INVENTION

A new estimator for finding the velocity transverse to the ultrasound beam has been developed. The estimator takes into account the influence from the axial velocity both through a subtraction of phase shifts and through tracking as described below under the headline Using Axial Velocity Compensation. Tracking is done between consecutive lines to minimize the axial range of tracking, and thereby minimize the effect of velocity dispersion. The estimator also partly compensates for the difference in the modulation period of the axial and transverse modulation by incorporating a lag different from 1 as used in the traditional autocorrelation approach. The effect of noise is taken into account through averaging RF samples over the pulse length. Estimating the actual center frequency before averaging also takes into account the effect from attenuation. The new estimator is unbiased since the actual mean modulation frequency of the transverse field is estimated before being applied in the estimator. This can be done since the estimator finds the mean velocity in the transverse direction.

Measurement of Transverse Velocities

Conventional velocity estimation systems measure or estimate axial velocity only. By axial velocity is understood the component of the velocity vector in the direction of propagation of ultrasound energy from the ultrasound transducer. In the conventional systems the measurement is performed by emitting a sinusoidal ultrasound pulsed field in one direction a number of times. The returned signal is then sampled at the depth of interest do. The sampled signal for a nearly monochromatic pulse is given by [7]

$$r(i) = \cos\left(2\pi \frac{2v_z}{c} f_0 i T_{prf} + \phi\right) \quad (1)$$

where c is the speed of sound, $v_z$ the blood velocity component in the ultrasound direction, $f_0$ the emitted center frequency, i the pulse number, $T_{prf}$ the time between pulse emissions, and $\phi$ is an arbitrary phase factor that depends on the depth. The frequency of the returned signal $$f_p = \frac{2v_z}{c} f_0 \quad (2)$$

is, thus, proportional to the blood velocity, and can be estimated as either a mean frequency in the spectrum of the received signal or a phase shift.

Velocity transverse to the ultrasound beam cannot be estimated from the sampled signal, and a signal influenced by the transverse velocity must be used. The underlying mechanism making it possible to perform axial velocity estimation is the oscillations in the emitted signal. Introducing a transverse spatial oscillation in the ultrasound field causes the transverse velocity to influence the received signal as described in [5] and [6]. The received signal can then be written as:

$$r_t(i) = \cos(2\pi f_p i T_{prf}) \cos\left(2\pi \frac{v_x}{d_x} i T_{prf}\right) \quad (3)$$

where $v_x$ is the transverse velocity and $d_x$ is the lateral modulation period. The frequency due to the transverse motion can then be written $$f_x = \frac{v_x}{d_x} \quad (4)$$

Such an approach has been suggested in [6], [5], [8].

The velocities can be both positive and negative and a signal with a one-sided spectrum should be employed to probe the region of interest. This can be found by performing a Hilbert transform on the signals, and for the axial velocity estimation the sampled signal is then $$r_q(i) = \exp\left(j2\pi\frac{2v_z}{c}f_0 iT_{prf} + \phi\right) \quad (5)$$

A spatial Hilbert transform must be employed, when finding the transverse velocity, and this can be approximated by having two parallel probing beams displayed a distance $d_x/4$ to yield the spatial quadrature field.

Derivation of the Estimator

The received and sampled in phase spatial quadrature field can be written as $$r_{sq}(i) = \cos(2\pi f_p i T_{prf})\exp(j2\pi f_x i T_{prf}) \quad (6)$$

assuming that both the temporal and spatial fields are monochromatic and of unit amplitude. The received field is, thus, influenced by both the axial and the transverse velocity. The influence from the axial velocity on the transverse estimate has previously been compensated for by using tracked data, but any error in tracking due to a poor axial velocity estimate can influence the transverse velocity estimation.

Basic Estimator

The axial velocity compensation by tracking can be avoided by employing the more advanced estimator developed in this section.

The temporal Hilbert transform of (6) yields the temporal quadrature spatial quadrature field signal:

$$r_{sqh}(i) = \sin(2\pi f_p i T_{prf})\exp(j2\pi f_x i T_{prf}) \quad (7)$$

Rewriting (6) and (7) using Euler's equations gives $$r_{sq} = \frac{1}{2}(\exp(j2\pi i T_{prf}(f_x - f_p)) + \exp(j2\pi i T_{prf}(f_x - f_p))) \quad (8)$$

$$r_{sqh} = \frac{1}{2}(\exp(j2\pi i T_{prf}(f_x + f_p)) - \exp(j2\pi i T_{prf}(f_x - f_p)))$$

Two new signals are then formed from $$r_1 = r_{sq}(i) + jr_{sqh}(i) = \quad (9)$$
$$\frac{1}{2}(\exp(j2\pi i T_{prf}(f_x + f_p)) + \exp(j2\pi i T_{prf}(f_x - f_p))) +$$
$$j\frac{1}{2j}(\exp(j2\pi i T_{prf}(f_x - f_p)) - \exp(j2\pi i T_{prf}(f_x - f_p))) =$$
$$\exp(j2\pi i T_{prf}(f_x + f_p))$$

$$r_2 = r_{sq}(i) - jr_{sqh}(i) = \quad (10)$$
$$\frac{1}{2}(\exp(j2\pi i T_{prf}(f_x - f_p)) + \exp(j2\pi i T_{prf}(f_x - f_p))) -$$
$$j\frac{1}{2j}(\exp(j2\pi i T_{prf}(f_x + f_p)) - \exp(j2\pi i T_{prf}(f_x - f_p))) =$$
$$\exp(j2\pi i T_{prf}(f_x - f_p))$$

Finding the changes in phase as a function of sample number for the two signals give:

$$d\Theta_1 = \frac{\Delta\Theta_1}{\Delta i} = 2\pi T_{prf}(f_x + f_p) \quad (11)$$

$$d\Theta_2 = \frac{\Delta\Theta_2}{\Delta i} = 2\pi T_{prf}(f_x - f_p)$$

Adding the two phase changes gives $$d\Theta_1 + d\Theta_2 = 2\pi 2 T_{prf} f_x = 4\pi T_{prf}\frac{v_x}{d_x} \quad (12)$$

and subtracting them gives $$d\Theta_1 - d\Theta_2 = 2\pi 2 T_{prf} f_p = 4\pi T_{prf}\frac{2v_x}{c}f_x \quad (13)$$

The transverse velocity can thus be found directly from:

$$v_x = \frac{(d\Theta_1 + d\Theta_2)d_x}{2\pi 2 T_{prf}} \quad (14)$$

and the axial velocity from $$v_x = \frac{(d\Theta_1 + d\Theta_2)c}{2\pi 4 T_{prf} f_0} \quad (15)$$

The combination of signals, thus, makes it possible to automatically compensate for the axial and transverse movements, respectively. This is especially important for the transverse estimation due to the rapid variation in phase for an axial movement compared to a transverse movement. An alternative to (15) is to find the axial velocity through a traditional estimator by forming a received beam with conventional beam forming without the transverse modulation. This can potentially yield a higher precision at the expense of an extra receive beam former.

An alternative to combining the signals in (10) would be to find the autocorrelation functions of the two signals and then perform the subtraction or addition on the autocorrelations. The velocity components are then found from the phase shifts in the combined autocorrelations.

The determination of the phase changes for the complex signal can, eg, be-done using the standard autocorrelation estimator [9], [7]. Having the complex signal $$r(i) = x(i) + jy(i) \quad (16)$$

the phase change is determined by $$d\bar{\theta} = \arctan\left(\frac{\sum_{i=0}^{N-1} y(i)x(i-1) - y(i-1)x(i)}{\sum_{i=0}^{N-1} x(i)x(i-1) + y(i)y(i-1)}\right) \quad (17)$$

Using the estimated complex autocorrelation of the signal $$\bar{R}(m) = \frac{1}{N-m}\sum_{i=0}^{N-m} r^*(i)r(i+m) \quad (18)$$

this can also be stated as $$d\bar{\Theta} = \arctan\left(\frac{\mathcal{J}\{R(1)\}}{\mathcal{R}\{R(1)\}}\right) \quad (19)$$

where $\mathcal{J}\{R(1)\}$ denotes the imaginary part of the complex autocorrelation, $\mathcal{R}\{R(1)\}$ the real part, and 1)1 is the lag in the autocorrelation. This is equivalent to finding the mean frequency in the power density spectrum given by [7]

$$\bar{f} = \frac{\int_{-fprf}^{fprf/2} fP(f)df}{\int_{-fprf}^{fprf/2} fP(f)df} \quad (20)$$

where $R(m) \leftrightharpoons P(f)$ from which the axial velocity is determined by $$v_z = \frac{c}{2} \cdot \frac{\bar{f}}{f_0} \quad (21)$$

This estimator, thus, finds the mean velocity. The estimator is also unbiased for white noise added to the input signal r (i) [7].

Finding the phase change by (17) entails finding the arctan of the argument, and the transverse velocity estimation through (14), thus, depends on two arctangents. This creates problems when the phase aliases and a better calculation can be found from using the relation $$\tan(A+B) = \frac{\tan(A) + \tan(B)}{1 - \tan(A)\tan(B)} \text{ then} \quad (22)$$

$$\tan(d\Theta_1 + d\Theta_2) = \tan\left(\arctan\left(\frac{\mathcal{J}\{R_1(1)\}}{\mathcal{R}\{R_1(1)\}}\right) + \arctan\left(\frac{\mathcal{J}\{R_2(1)\}}{\mathcal{R}\{R_2(1)\}}\right)\right) \quad (23)$$

$$= \frac{\frac{\mathcal{J}\{R_1(1)\}}{\mathcal{R}\{R_1(1)\}} \frac{\mathcal{J}\{R_2(1)\}}{\mathcal{R}\{R_2(1)\}}}{1 - \frac{\mathcal{J}\{R_1(1)\}}{\mathcal{R}\{R_1(1)\}} \frac{\mathcal{J}\{R_2(1)\}}{\mathcal{R}\{R_2(1)\}}}$$

$$= \frac{\mathcal{J}\{R_1(1)\}\mathcal{R}\{R_2(1)\} + \mathcal{J}\{R_2(1)\}\mathcal{R}\{R_1(1)\}}{\mathcal{R}\{R_1(1)\}\mathcal{R}\{R_2(1)\} - \mathcal{J}\{R_1(1)\}\mathcal{J}\{R_2(1)\}}$$

where $R_1(1)$ is the complex lag one autocorrelation value for $r_1(i)$ and $R_2(1)$ is the complex lag one autocorrelation value for $r_2(i)$ A similar expression can be derived for the axial velocity, and the estimators are:

$$v_x = \frac{d_x}{2\pi 2 T_{prf}} \arctan\left(\frac{\mathcal{J}\{R_1(1)\}\mathcal{R}\{R_2(1)\} + \mathcal{J}\{R_2(1)\}\mathcal{R}\{R_1(1)\}}{\mathcal{R}\{R_1(1)\}\mathcal{R}\{R_2(1)\} - \mathcal{J}\{R_1(1)\}\mathcal{J}\{R_2(1)\}}\right) \quad (24)$$

and $$v_z = \frac{c}{2\pi 4 T_{prf} f_0} \arctan\left(\frac{\mathcal{J}\{R_1(1)\}\mathcal{R}\{R_2(1)\} - \mathcal{J}\{R_2(1)\}\mathcal{R}\{R_1(1)\}}{\mathcal{R}\{R_1(1)\}\mathcal{R}\{R_2(1)\} + \mathcal{J}\{R_1(1)\}\mathcal{J}\{R_2(1)\}}\right) \quad (25)$$

These two new estimators compensate for the phase shift in the transverse direction to the velocity component estimated by using fourth order moments compared to the second order estimator used in [6].

Compensation for Different Wavelengths

The lateral modulation period will in general be larger than the wavelength of the probing ultrasound pulse. For a given velocity the change in phase for the transverse signal will, thus, be smaller than the change in phase for the axial signal. Optimizing the pulse repetition time for both measurements simultaneously is therefore not possible, and a larger change in phase for the transverse motion must be artificially introduced. This can be attained by using a lag different from one in the autocorrelation estimator as $$d\hat{\Theta} = \frac{1}{k}\arctan\left(\frac{\mathcal{J}\{R(k)\}}{\mathcal{R}\{R(k)\}}\right) \quad (26)$$

$$\hat{R}(k) = \frac{1}{N-k}\sum_{i=0}^{N-k} r^*(i)r(i+k)$$

which can be directly used in (24) and (25).

Using the condition that the phase shift should be the same for $v_x = v_z$, the lag can be roughly determined by:

$$k \approx \frac{d_x}{\lambda} \quad (27)$$

$$\lambda = \frac{c}{f_0}$$

Often this equation will give a large value for k, and the calculation of the autocorrelation in (26) will include too few values for a low variance estimate. A compromise can be attained by reducing k to obtain both a larger phase shift and a sufficient number of data values for the calculation of $\hat{R}(k)$ Optimization in the Case of Noise and Attenuation The scattering of ultrasound form blood is weak, and a poor signal-to-noise ratio is often found after stationary echo canceling. A prime concern is therefore to make the estimator robust in a noisy environment. This can be attained by averaging the autocorrelation estimate over the length of the interrogating pulse corresponding to performing a matched filtration. The length of the pulse in terms of RF samples is given by $$N_p = \frac{M}{f_0} f_s \quad (28)$$

where M is the number of periods in the pulse (typically 4 to 8) and $f_s$ is the sampling frequency. The autocorrelation estimate is then calculated by $$\bar{R}(k) = \frac{1}{(N-k)N_p}\sum_{i=0}^{N-k}\sum_{n=-N_p/2}^{N_p/2-1} r^*(i, n+N_0)r(i+k, n+N_0) \quad (29)$$

Here r(i,ii) denotes the received signal for the i'th line and its ii'th RF sample. No is the sample number for the position of the velocity estimation, and the averaging is done symmetrically around this position to reduce the effects of velocity dispersion.

The center frequency, $f_0$ of the ultrasound pulse will change as a function of depth due to the frequency dependent attenuation of the tissue. The number of samples $N_p$ should therefore also changer. The actual mean center frequency can be determined by $$\bar{f}_0(z) = \frac{\int_{-f_s/2}^{f_s/2} f P_{rf}(f, z) df}{\int_{-f_s/2}^{f_s/2} P_{rf}(f, z)} \quad (30)$$

where $f_s$ is the sampling frequency, z is the depth of interest, and $P_{rf}(f,z)$ is the spectrum of the received RF signal around the depth z. $\bar{f}_{sr}(z)$ can then be used in (28) to fit the filtration to the measurement situation.

Using Axial Velocity Compensation

The estimation process can also be optimized by partially compensating for the axial velocity, when doing the transverse velocity estimation. This can easily be done since the developed estimator essentially subtracts out the phase shift from the axial motion during the transverse estimation process. Whether this is the actual velocity or a smaller phase shift is of no importance. Also the autocorrelation estimator finds the phase shift from one line to the next and therefore a fixed phase shift or equivalently delay can be used. The autocorrelation estimator is then given by.

$$\vec{R}(k) = \quad (31)$$

$$\frac{1}{(N-k)N_p} \sum_{i=0}^{N-k} \sum_{n=-N_p/2}^{N_p/2-1} r^*(i, n + N_0 - n_s/2) r(i+k, n + N_0 + n_s/2)$$

where $n_s$ is the axial movement compensation delay given by $$n_s = \text{round}\left(k \frac{2v_z}{c} T_{prf} f_s\right) \quad (32)$$

rounded off to the nearest number of samples. This ensures that the estimator has the smallest phase shift from the axial movement to compensate for.

Estimating the Lateral Modulation Period

The transverse velocity estimate is directly proportional to the lateral modulation period, and a wrong modulation period gives rise to a biased estimate.

Figure 2:
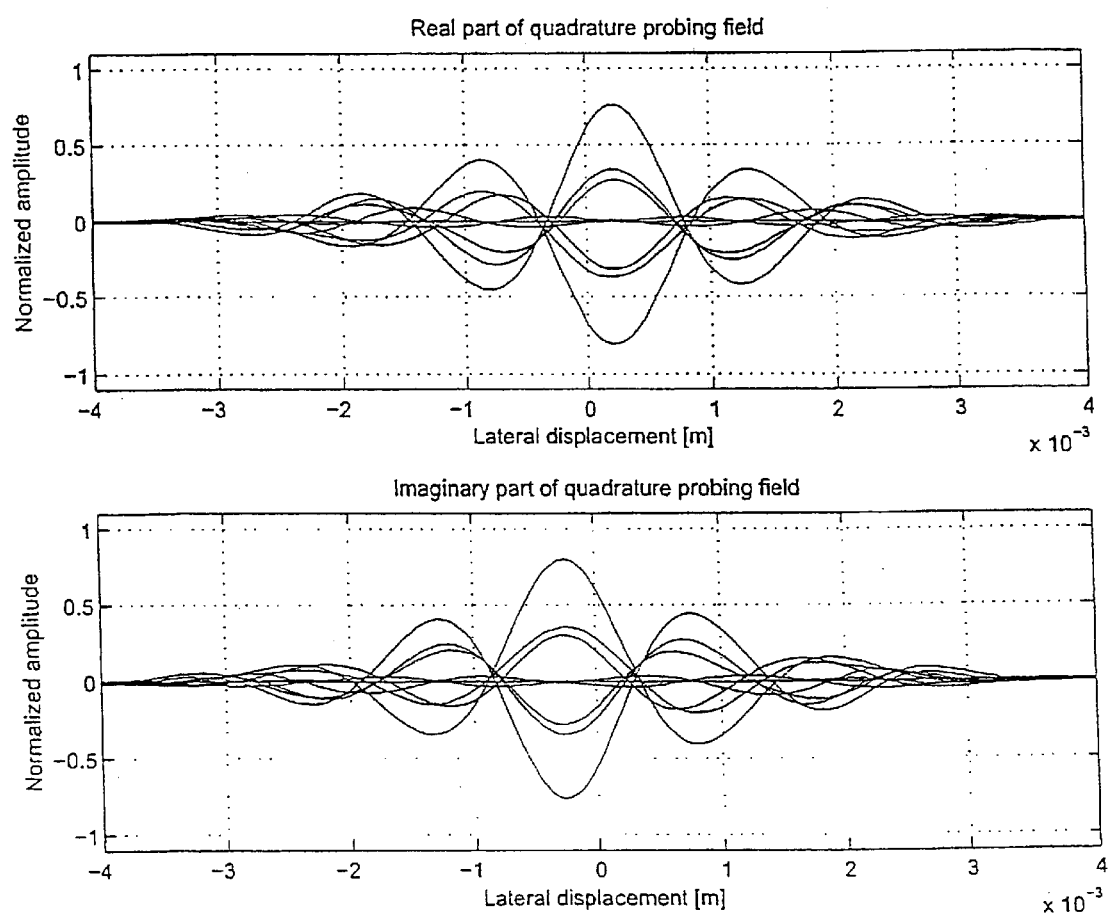

The lateral modulation does not have so sharply defined a band pass spectrum as found for the axial pulse. This can be seen from FIGS. 2 and 3. The autocorrelation method, however, estimates the mean frequency, and an estimate of the mean modulation period can, thus, be used to ensure unbiased estimates. This is obtained by first simulating or measuring both the in-phase and quadrature field from a point scatterer moving in front of the transducer at the depth of interest. The spatio-temporal Fourier transform $H(f_{time}, f_{space})$ of the complex probing field is then found as shown on FIG. 3.

The real part of the transformed signal is the in-phase field and the imaginary part is the quadrature component. The spectrum is approximately one sided due to the Hilbert transform relation between the real and imaginary part of the signal. The mean spatial frequency can be then be found from.

$$\bar{f}_{space} = \frac{\int_{-f_s/2}^{+f_s/2} \int_{-f_{sx}/2}^{+f_{sx}/2} f_{space} |H(f_{time}, f_{space})|^2 df_{time} df_{space}}{\int_{-f_s/2}^{+f_s/2} \int_{-f_{sx}/2}^{+f_{sx}/2} |H(f_{time}, f_{space})|^2 df_{time} df_{space}} \quad (33)$$

assuming that the scattering signal from blood has a white spectrum and is homogeneous over the interrogated region. Here $f_{sx}$ is the lateral spatial sampling frequency. The mean lateral modulation period is then $$\bar{d}_x = \frac{1}{\bar{f}_{space}} \quad (34)$$

Figure 3:
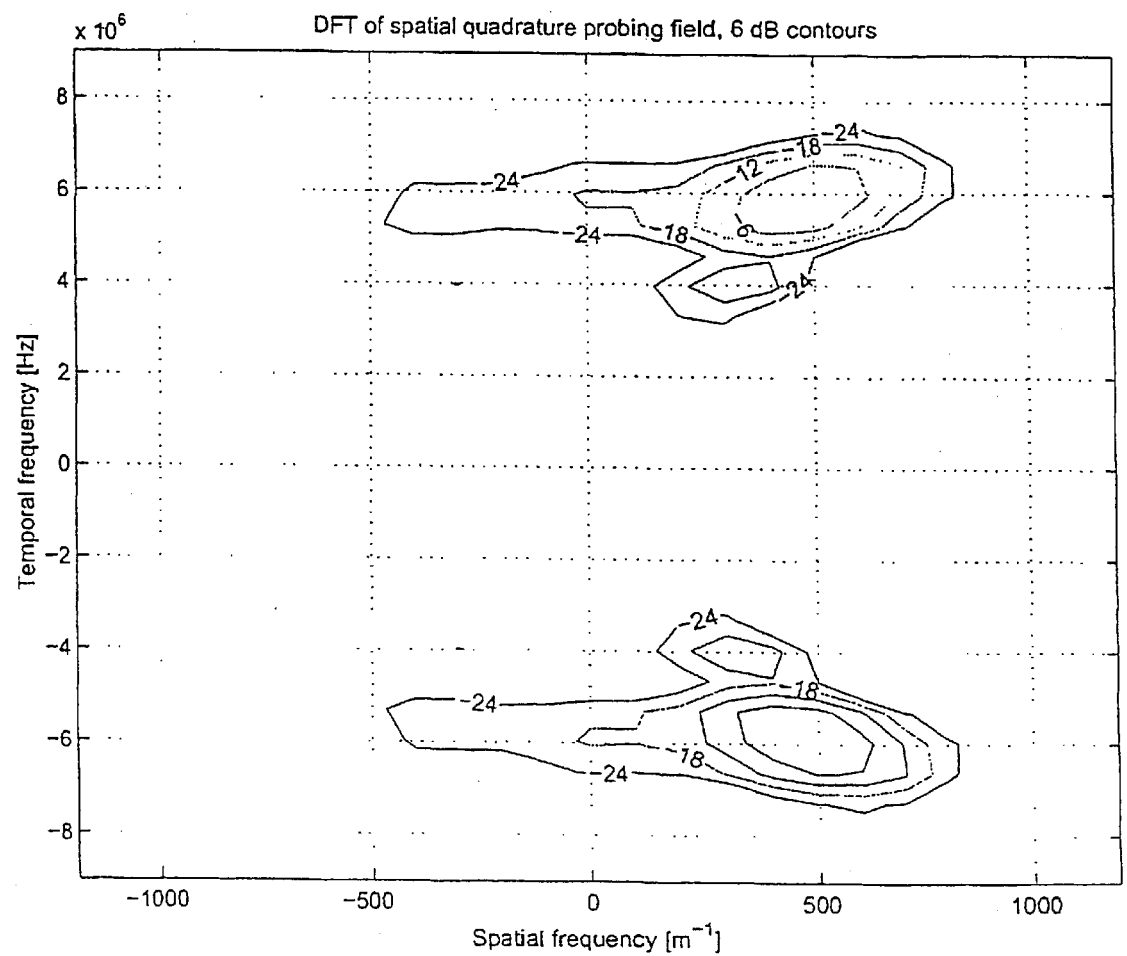

FIG. 3 and (33) also indicate how to optimize the measurement field. Ideally a narrow band, single-sided spectrum should be used for having a well-defined measurement situation and thereby a precise velocity estimate. A measure of the spectral spread is obtained by.

$$\sigma^2[i] = \frac{\int_{-f_s/2}^{+f_s/2} \int_{-f_{sx}/2}^{+f_{sx}/2} (f_{space} - \bar{f}_{space})^2 |H(f_{time}, f_{space})|^2 df_{time} df_{space}}{\int_{-f_s/2}^{+f_s/2} \int_{-f_{sx}/2}^{+f_{sx}/2} |H(f_{time}, f_{space})|^2} \quad (35)$$

This can form the basis for the optimization of the spatial quadrature field and the lowest possible value for $\sigma^2_{jspace}$ will give the best result.

FUNCTIONALITY OF THE INVENTION

Figure 4:
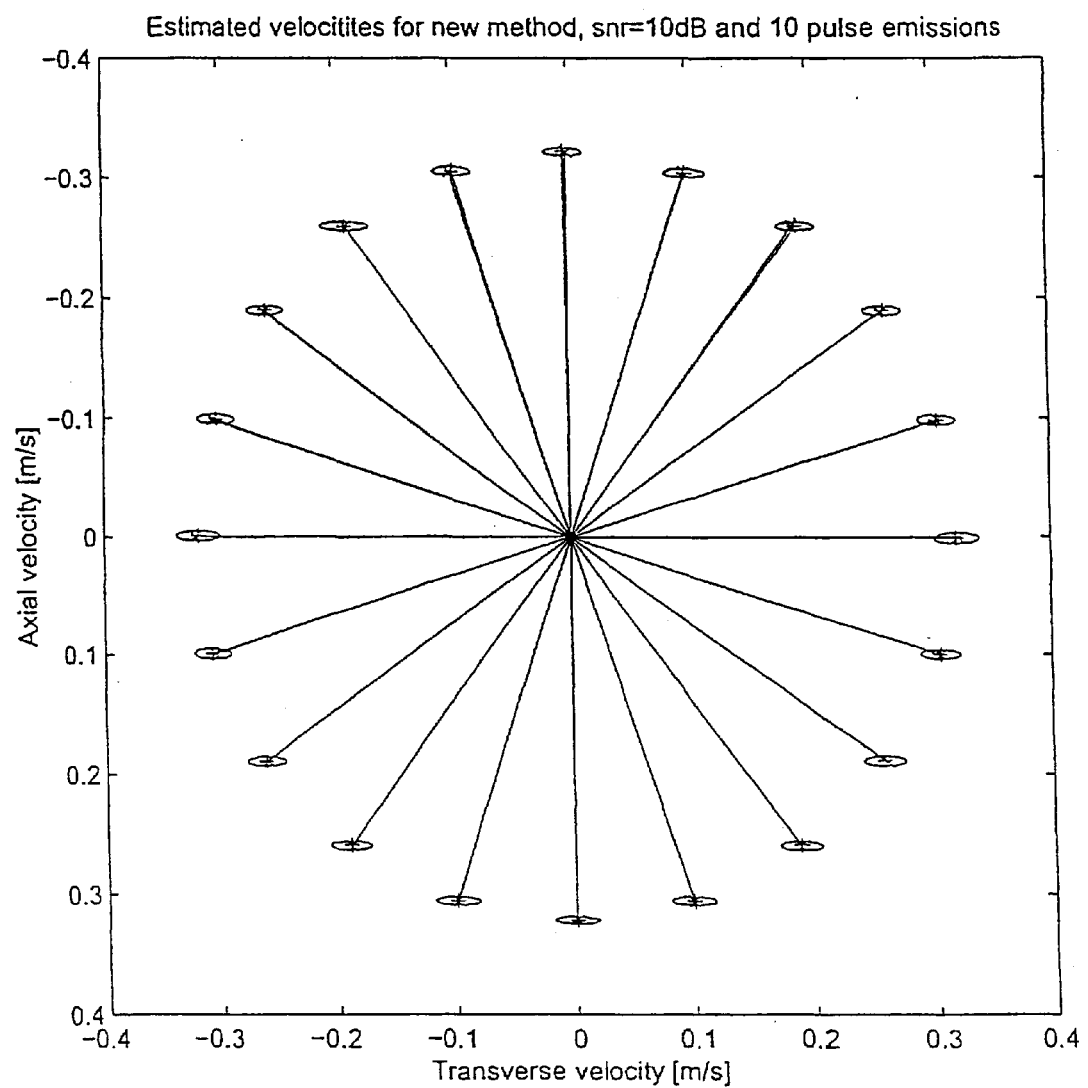

The first example in FIG. 4 shows the performance of the new estimator for a purely monochromatic field, where the field is given by equation (6). The lines from origo to '+' indicates the true velocities. The lines from origo to 'x' indicate the respective mean values of all the estimates. The ellipses each represent one standard deviation of the estimates in both the transverse and axial direction. The simulation parameters are given in Table 1. Gaussian white noise has been added to the signals. It is seen that the estimator correctly finds the velocity without error. No axial velocity compensation is used in the estimator for this plot, but a similar performance is obtained with axial velocity compensation.

In the second example a pulsed field generated by the Field 11 simulation program described in [10] and [11] is used. This field has been convolved with a two-dimensional random, Gaussian signal for generating a signal with speckle characteristics. The received radio frequency (RF) signals are then generated by selecting the appropriate data from this two-dimensional image according to the transverse and axial velocities. The signals are then shifted an integer number of samples between pulse emissions. The simulation parameters are given in Table 2.

Figure 5:
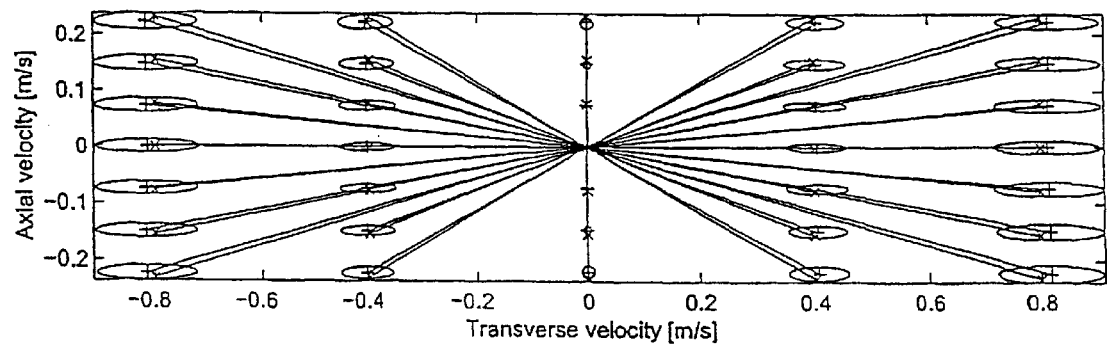

The results of the simulation in the second example are shown in FIG. 5 for a signal-to-noise ratio of 20 dB, and for 100 different estimates. The axial velocity was found through the normal autocorrelation estimation with RF averaging, and the new estimator was used for the transverse velocity. Axial velocity compensation as described was used in the new estimator.

Figure 6:
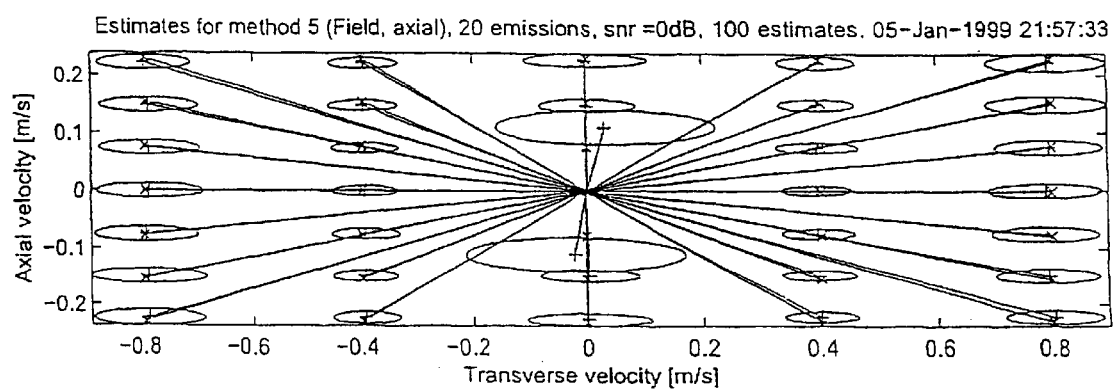

Increasing the noise to yield as signal-to-noise ratio of 0 dB gives the results shown in FIG. 6. Satisfactory results are still seen at this low signal to noise ratio.

Figure 7:
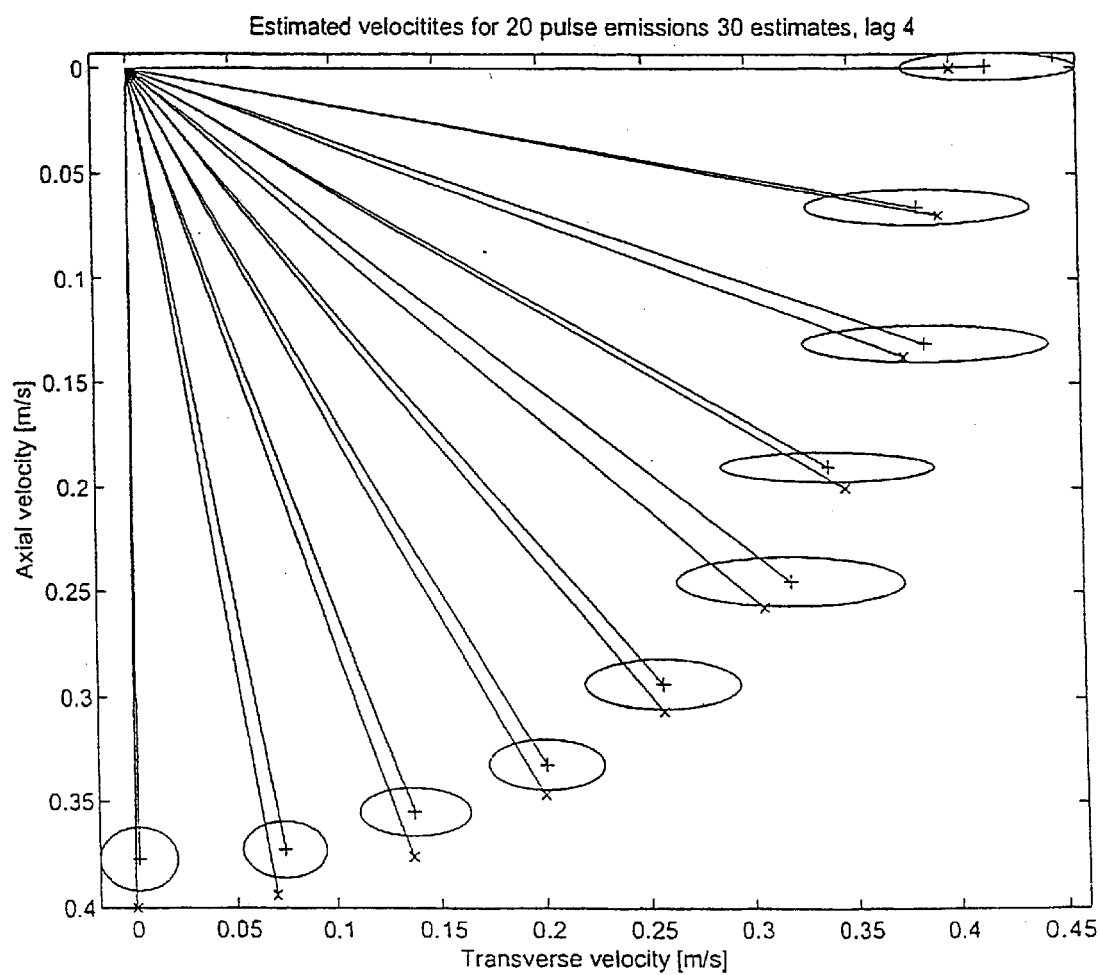

To avoid moving an integer number of samples in the venerated speckle pattern, a full Field 11 simulation has been made using roughly 35,000 point-scatterers. The same parameters as before are used. Making plug flow estimation for different angles gives the estimates shown in FIG. 7. No noise has been added to these data, but similar results are obtained for signal-to-noise ratios above 10 dB.

Figure 8:
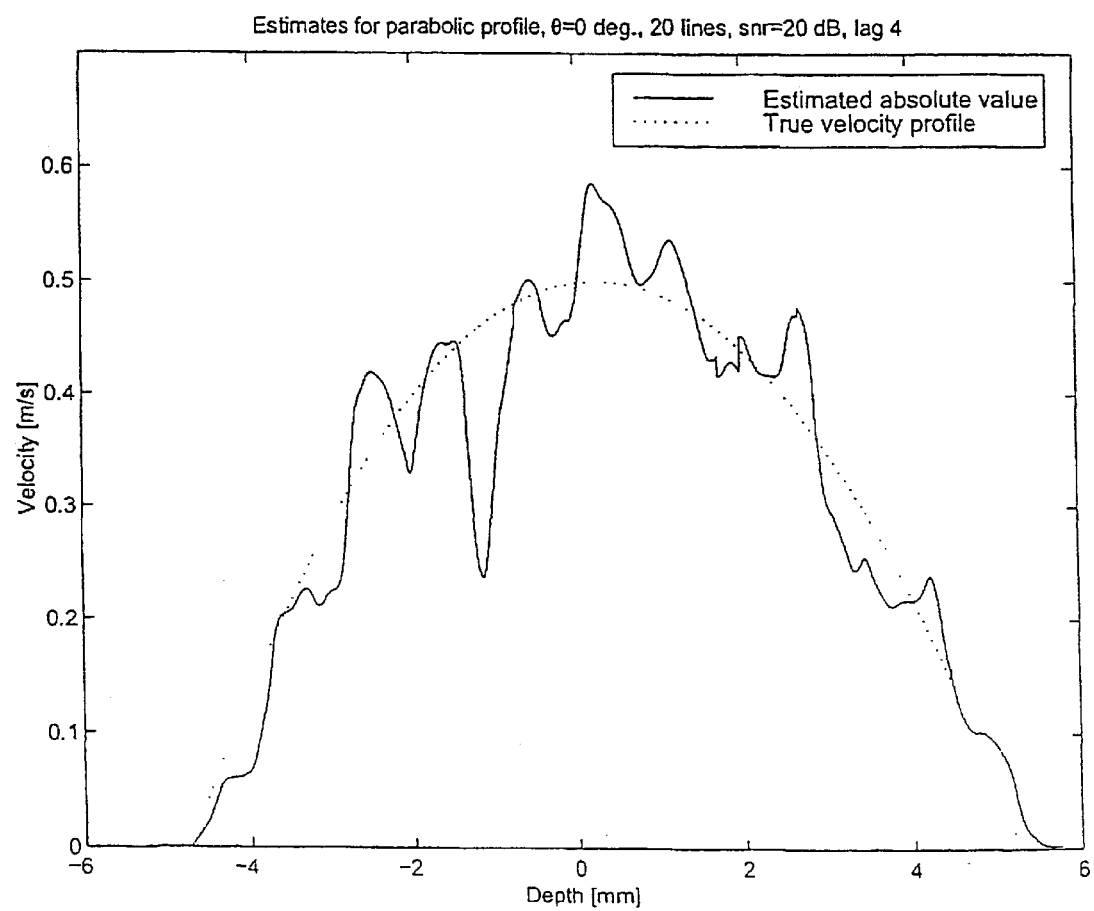
Figure 9:
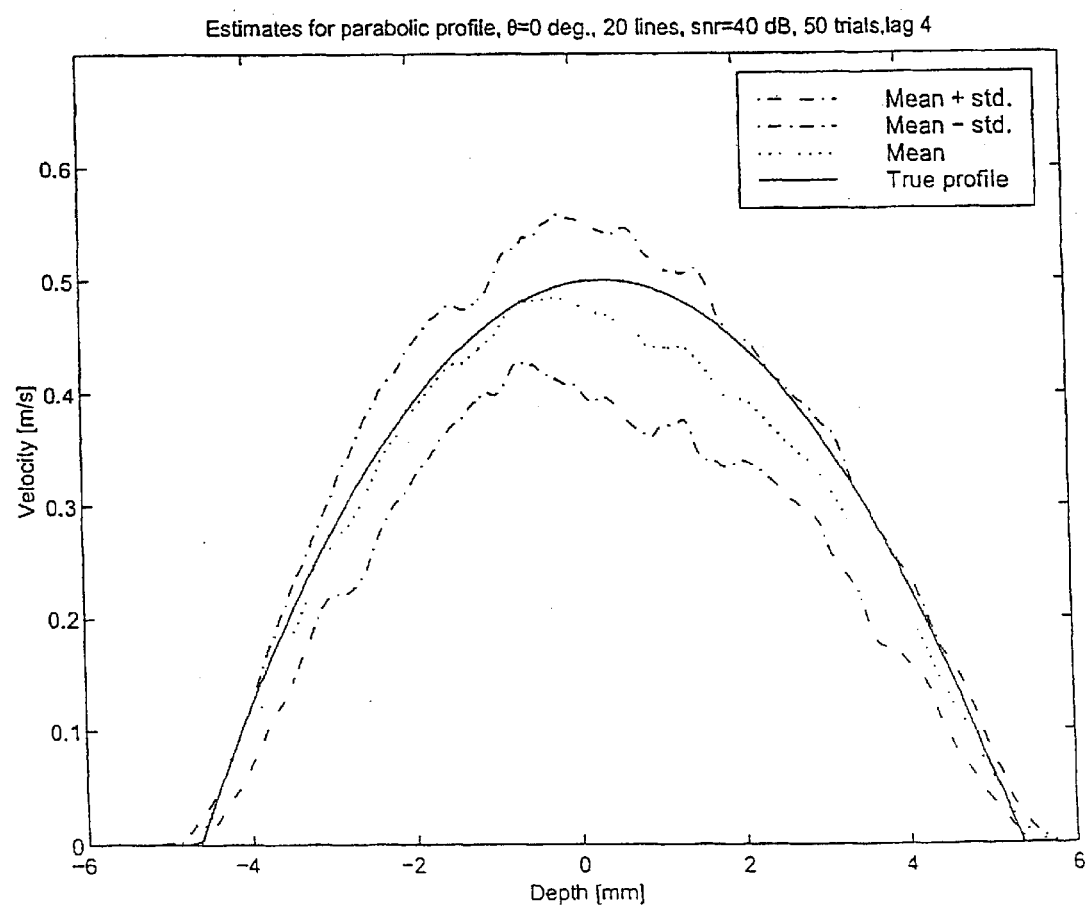

A full simulation with a parabolic flow profile using 36,000 point-scatterers was performed for a vessel with a radius of 5 mm. The peak velocity was 0.5 m/s, and the vessel was perpendicular to the ultrasound beam. A conventional color flow mapping system would in this situation show a velocity of 0 m/s and, thus, show that no velocity is present at this position in the image. The estimates from the new method are shown in FIG. 8. Gaussian noise has been added to the simulation result to obtain a signal-to-noise ratio of 20 dB otherwise the same parameters as before are used. The true velocity profile is shown as the dashed line. Comparing with this the standard deviation of the result is 0.050 m/s, and the mean deviation of the whole profile is −0.0067 m/s. The standard deviation relative to the maximum velocity is 10.1%. FIG. 9 shows when the simulation has been repeated 50 times. The mean value±one standard deviation is shown.

REFERENCES

[1] D. J. Phillips, K. W. Beach, and J. Primozich D. E. Strandness. Should results of ultrasound Doppler studies be reported in units of frequency or velocity? *Ultrasound Med. Biol.*, 15:205–212, 1989.

[2] M. D. Fox. Multiple crossed-beam ultrasound Doppler velocimetry. *IEEE Trans. Son. Ultrason.*, SU-25:281–286, 1978.

[3] G. E. Trahey, J. W. Allison, and O. T. von Ramm. Angle independent ultrasonic detection of blood flow. *IEEE Trans. Biomed. Eng.*, BME-34:965–967, 1987.

[4] V. L. Newhouse, D. Censor, T. Vontz, J. A. Cisneros, and B. B. Goldberg. Ultrasound Doppler probing of flows transverse with respect to beam axis. *IEEE Trans. Biomed. Eng.*, BNE-34:779–788, 1987.

[5] J. A. Jensen and P. Munk. A new method for estimation of velocity vectors. IEEE Trans. Ultrason., Ferroelec., Freq. Contr., 45:837–851, 1998.

[6] Apparatus and method for determining movements and velocities of moving objects, International patent application, publication number WO 98/00719, published 8 Jan. 1998.

[7] J. A. Jensen. *Estimation of Blood Velocities Using Ultrasound: A Signal Processiiug Approach.* Cambridge University Press, New York, 1996.

[8] P. Munk and J. A. Jensen. Performance of a vector velocity estimator. In *Proc. IEEE Ultrason. Symp.*, pages 1489–1493, 1998.

[9] C. Kasai, K. Namekawa, A. Koyano, and R. Omoto. Real-time two-dimensional blood flow imaging using an autocorrelation technique. *IEEE Trans. Son. Ultrason.*, 32:458–463, 1985.

[10] J. A. Jensen and N. B. Svendsen. Calculation of pressure fields from arbitrarily shaped, apodized, and excited ultrasound transducers. *IEEE Trans. Ultrason. Ferroelec., Freq. Contr.*, 39:262–267, 1992.

[11] J. A. Jensen. Field: A program for simulating ultrasound systems. Med. Biol. Eng. Comp., 10th Nordic-Baltic Conference oil Biomedical Imaging, Vol. 4, Supplement 1, Part 1:351–353, 1996b.

TABLE 1

Simulation parameters for monochromatic simulation.

| Parameter | Value |
|---|---|
| $f_s$ | 50 MHz |
| $f_0$ | 3 MHz |
| M | 4 |
| $d_x$ | 2 mm |
| $T_{prf}$ | 100 µs |
| N | 10 |
| snr | $\sqrt{10}$ |
| Lag compensation k | 4 |

TABLE 2

Simulation parameters for simulations using the Field II simulation program.

| Parameter | Value |
|---|---|
| $f_s$ | 100 MHz |
| $f_0$ | 6 MHz |
| M | 4 |
| $\overline{d}_x$ | 2.26 mm |
| $T_{prf}$ | 100 µs |
| N | 20 |
| snr | 10 |
| Lag compensation k | 4 |
| Transducer elements | 128 |
| Transducer element width | λ/2 |
| Transducer element height | 5 mm |
| Transducer element kerf | λ/10 |
| Transmit focus | 70 mm |
| Transmit apodization | van Hann window |
| Receiver focus | fixed at 38.5 mm |
| Receiver apodization | double sinc |
| Center of vessel | 38.5 mm |

What is claimed is:

1. An apparatus for measuring the velocity of a moving object or a collection of moving objects, the apparatus comprising:

a generator for generating pulses of excitation signals, an emitting transducer for transforming said excitation signals into a beam of wave energy and for emitting said wave energy in a predetermined direction of propagation, a receiving transducer for receiving signals from said moving object or objects generated by interaction with said wave energy emitted from said emitting transducer, wherein said emitting transducer and said receiving transducer having respective sensitivities which in combination give a resulting sensitivity oscillating spatially in a direction transverse to said direction of propagation, wherein the velocity component transverse to the beam is estimated using $$v_x = \frac{d_x}{2\pi k 2 T_{prf}} \arctan\left(\frac{\mathcal{J}\{R_1(k)\}\mathcal{R}\{R_2(k)\} + \mathcal{J}\{R_2(k)\}\mathcal{R}\{R_1(k)\}}{\mathcal{R}\{R_1(k)\}\mathcal{R}\{R_2(k)\} - \mathcal{J}\{R_1(k)\}\mathcal{J}\{R_2(k)\}}\right) \quad (36)$$

as an estimator,
and the axial velocity component along the beam is estimated using $$v_z = \frac{c}{2\pi k 4 T_{prf} f_0} \arctan\left(\frac{\mathcal{J}\{R_1(k)\}\mathcal{R}\{R_2(k)\} - \mathcal{J}\{R_2(k)\}\mathcal{R}\{R_1(k)\}}{\mathcal{R}\{R_1(k)\}\mathcal{R}\{R_2(k)\} + \mathcal{J}\{R_1(k)\}\mathcal{J}\{R_2(k)\}}\right) \quad (37)$$

as an estimator,
where $\mathfrak{I}\{R(k)\}$ denotes the imaginary part of the complex autocorrelation and $\mathfrak{I}\{R(k)\}$ the real part, and where $R_1(k)$ is the complex lag k autocorrelation value for the signal $r_1(i)$ given by $$r_1(i) = r_{sq}(i) + jr_{sqh}(i) \tag{38}$$

where $r_{sq}(i)$ is the received and sampled spatial quadrature field and $r_{sqh}(i)$ is the spatial Hilbert transform of $r_{sq}(i)$ and $R_2(1)$ is the complex lag one autocorrelation value for the signal $r_2(i)$ given by $$r_2(i) = r_{sq}(i) - jr_{sqh}(i), \tag{39}$$

where i denotes the pulse-echo line number, c is the speed of the wave energy, $f_0$ is the center frequency of the emitted wave energy, $d_x$ is a period of the lateral oscillation of the sensitivity, and $T_{prf}$ is the time between pulse emissions.

2. An apparatus according to claim 1 where a lag greater than one is used in the estimators.

3. An apparatus according to claim 1 where the received and sampled signal is summed as $$\hat{R}(k) = \frac{1}{(N-k)N_p} \sum_{i=0}^{N-k} \sum_{n=-N_p/2}^{N_p/2-1} r^*(i, n+N_0) r(i+k, n+N_0) \tag{40}$$

where r(i,n) denotes the signal for the i'th line and its n'th sample, $N_0$ is the sample number for the position of the velocity estimation, and $N_p$ is the number of samples in a segment.

4. An apparatus according to claim 1 where the center frequency is estimated using $$\bar{f}_0(z) = \frac{\int_{-f_s/2}^{f_s/2} f P_{rf}(f, z) df}{\int_{-f_s/2}^{f_s/2} P_{rf}(f, z) df} \tag{41}$$

as an estimator, where $f_s$ is the sampling frequency, z is the depth of interest, $P_{rf}(f,z)$ is the spectrum of the received signal around the depth z and f is the temporal frequency.

5. An apparatus according to claim 1 where the axial velocity component is compensated for by using $$\hat{R}(k) = \frac{1}{(N-k)N_p} \sum_{i=0}^{N-k} \sum_{n=-N_p/2}^{N_p/2-1} r^*(i, n+N_0 - n_s/2) r(i+k, n+N_0 + n_s/2) \tag{42}$$

where $n_s$ is the axial movement compensation delay given by $$n_s = \text{round}\left(k \frac{2v_z}{c} T_{prf} f_s\right) \tag{43}$$

for the calculation of the autocorrelation.

6. An apparatus according to claim 1 where the transverse, modulation frequency used in the velocity estimator is found according to $$\bar{f}_{space} = \frac{\int_{-f_s/2}^{+f_s/2} \int_{-f_{sx}/2}^{+f_{sx}/2} f_{space} |H(f_{time}, f_{space})|^2 df_{time} df_{space}}{\int_{-f_s/2}^{+f_s/2} \int_{-f_{sx}/2}^{+f_{sx}/2} |H(f_{time}, f_{space})|^2 df_{time} df_{space}} \tag{44}$$

where $f_{sx}$ is the lateral spatial sampling frequency and $H(f_{time}, f_{space})$ is the spatio-temporal Fourier transform of the complex excitation signals.

7. A method of estimating the velocity of a moving object or a collection of moving objects, the method comprising emitting an excitation signal of pulses of wave energy as a beam in a predetermined direction of propagation, whereby at least part of the wave energy will interact with the moving object or collection of moving objects, receiving, from said moving object or objects, reflected signals resulting from interaction of emitted wave energy with the moving object or collection of moving objects, wherein the emission of the excitation signal and the reception of reflected signals have respective sensitivities which in combination give a resulting sensitivity oscillating spatially in a direction transverse to the direction of propagation, estimating the velocity component transverse to the predetermined direction, using $$v_x = \frac{d_x}{2\pi k 2 T_{prf}} \arctan\left(\frac{\mathcal{I}\{R_1(k)\}\mathcal{R}\{R_2(k)\} + \mathcal{I}\{R_2(k)\}\mathcal{R}\{R_1(k)\}}{\mathcal{R}\{R_1(k)\}\mathcal{R}\{R_2(k)\} - \mathcal{I}\{R_1(k)\}\mathcal{I}\{R_2(k)\}}\right) \tag{36}$$

as an estimator, and
estimating the axial velocity component along the predetermined direction using $$v_z = \frac{c}{2\pi k 4 T_{prf} f_0} \arctan\left(\frac{\mathcal{I}\{R_1(k)\}\mathcal{R}\{R_2(k)\} - \mathcal{I}\{R_2(k)\}\mathcal{R}\{R_1(k)\}}{\mathcal{R}\{R_1(k)\}\mathcal{R}\{R_2(k)\} + \mathcal{I}\{R_1(k)\}\mathcal{I}\{R_2(k)\}}\right) \tag{37}$$

as an estimator,
where $\mathfrak{I}\{R(k)\}$ denotes the imaginary part of the complex autocorrelation and $\mathfrak{R}\{R(k)\}$ the real part, and where $R_1(k)$ is the complex lag k autocorrelation value for the signal $r_1(i)$ given by $$r_1(i) = r_{sq}(i) + jr_{sqh}(i) \tag{38}$$

where $r_{sq}(i)$ is the received and sampled spatial quadrature field and $r_{sqh}(i)$ is the spatial Hilbert transform of $r_{sq}(i)$ and $R_2(1)$ is the complex lag one autocorrelation value for the signal $r_2(i)$ given by $$r_2(i) = rsq(i) - jr_{sqh}(i), \tag{39}$$

where i denotes the pulse-echo line number, c is the speed of the wave energy, $f_0$ is the center frequency of the emitted wave energy, $d_x$ is a period of the lateral oscillation of the sensitivity, and $T_{prf}$ is the time between pulse emissions.

8. A method according to claim 7 where the received and sampled signal is summed as $$\hat{R}(k) = \frac{1}{(N-k)N_p} \sum_{i=0}^{N-k} \sum_{n=-N_p/2}^{N_p/2-1} r^*(i, n+N_0) r(i+k, n+N_0) \tag{40}$$

where r(i,n) denotes the signal for the i'th line and its n'th sample, $N_0$ is the sample number for the position of the velocity estimation, and $N_p$ is the number of samples in a segment.

9. A method according to claim 7 where the center frequency is estimated using $$\bar{f}_0(z) = \frac{\int_{-f_s/2}^{f_s/2} f P_{rf}(f,z) df}{\int_{-f_s/2}^{f_s/2} P_{rf}(f,z) df} \quad (41)$$

as an estimator, where $f_s$ is the sampling frequency, z is the depth of interest, $P_r(f,z)$ is the spectrum of the received signal around the depth z and f is the temporal frequency.

10. A method according to claim 7 where the axial velocity component is compensated for by using $$\hat{R}(k) = \quad (42)$$

$$\frac{1}{(N-k)N_p} \sum_{i=0}^{N-k} \sum_{n=-N_p/2}^{N_p/2-1} r^*(i, n+N_0 - n_s/2) r(i+k, n+N_0 + n_s/2)$$

where $n_s$ is the axial movement compensation delay given by $$n_s = \text{round}\left(k \frac{2v_z}{c} T_{prf} f_s\right) \quad (43)$$

for the calculation of the autocorrelation.

11. A method according to claim 7 where the transverse modulation frequency used in the velocity estimator is found according to $$\bar{f}_{space} = \frac{\int_{-f_s/2}^{+f_s/2} \int_{-f_{sx}/2}^{+f_{sx}/2} f_{space} |H(f_{time}, f_{space})|^2 df_{time} df_{space}}{\int_{-f_s/2}^{+f_s/2} \int_{-f_{sx}/2}^{+f_{sx}/2} |H(f_{time}, f_{space})|^2 df_{time} df_{space}} \quad (44)$$

where $f_{sx}$ is the lateral spatial sampling frequency and $H(f_{time}, f_{space})$ is the spatio-temporal Fourier transform of the complex excitation signal.

* * * * *